United States Patent [19]

Regnier et al.

[11] Patent Number: 5,508,277
[45] Date of Patent: Apr. 16, 1996

[54] BICYCLIC PYRIMIDINES

[75] Inventors: Gilbert Regnier, Chatenay Malabry; Alain Dhainaut, Chatou; Ghanem Atassi, Saint Cloud; Alain Pierre, Marly Le Roi, all of France

[73] Assignee: Adir Et Compagnie, Courbevoie, France

[21] Appl. No.: 284,689

[22] PCT Filed: Dec. 9, 1993

[86] PCT No.: PCT/FR93/01211

§ 371 Date: Aug. 10, 1994

§ 102(e) Date: Aug. 10, 1994

[87] PCT Pub. No.: WO94/13668

PCT Pub. Date: Jun. 23, 1994

[30] Foreign Application Priority Data

Dec. 11, 1992 [FR] France .................................. 92 14913

[51] Int. Cl.⁶ ...................... C07D 473/16; C07D 487/04
[52] U.S. Cl. .................... 514/212; 514/211; 514/217; 514/258; 514/261; 514/266; 540/546; 540/547; 540/524; 544/254; 544/262; 544/264; 544/280
[58] Field of Search ........................ 544/262, 264, 544/280, 254; 514/258, 212, 266, 261

[56] References Cited

U.S. PATENT DOCUMENTS

| | | | |
|---|---|---|---|
| 4,100,286 | 7/1978 | Regnier | 544/262 |
| 4,212,866 | 7/1980 | Friebe | 514/266 |
| 5,079,249 | 8/1990 | Lavielle | 514/248 |
| 5,110,818 | 5/1992 | Allgeier | 544/264 |
| 5,204,353 | 4/1993 | Meier | 514/258 |
| 5,278,165 | 1/1994 | Janssens | 544/262 |
| 5,302,596 | 4/1994 | Oshima | 514/261 |
| 5,329,007 | 7/1994 | Peet | 544/262 |
| 5,397,782 | 3/1995 | Meert | 514/258 |

FOREIGN PATENT DOCUMENTS

| | | | |
|---|---|---|---|
| 495982 | 7/1992 | European Pat. Off. | 544/280 |
| 514542 | 11/1992 | European Pat. Off. | 544/258 |
| 94-13668 | 6/1994 | WIPO | 544/280 |

*Primary Examiner*—Donald G. Daus
*Attorney, Agent, or Firm*—Gordon W. Hueschen

[57] ABSTRACT

Novel bicyclic pyrimidine compounds for use as drugs and having formula (I). Said novel compounds and physiologically tolerable salts thereof may be used in therapeutics, particularly for suppressing tumour cell resistance to antineoplastic agents.

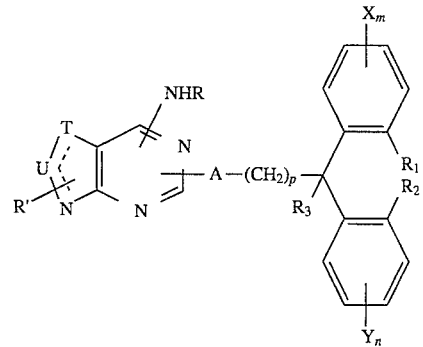

12 Claims, No Drawings

BICYCLIC PYRIMIDINES

This is a section 371 of PCT/FR93/01211, filed Dec. 9, 1993.

TECHNICAL FIELD

The present invention relates to new bicyclic pyrimidine compounds, a process for their preparation, and pharmaceutical compositions containing them.

PRIOR ART

The prior art in the pharmaceutical field is illustrated especially by published European Patent Applications Nos. 0.495 982 $A_1$ and 0 514 540 $A_1$, which relate to the compounds of formulae:

[Chemical structure]

and

[Chemical structure]

respectively, which formulae essentially differ from the compounds of the present invention in the meaning of the substituents —Y'—Z' and Y"—Z" on the pyrimidine nucleus, and in their pharmacological activity—the said products of the prior art being active against hypoxaemia associated with respiratory disorders whilst the compounds of the present invention partially or completely reverse the resistance of tumour cells to anti-cancer agents.

STATEMENT OF THE INVENTION

The invention relates especially to bicyclic pyrimidine compounds of formula I:

[Chemical structure (I)]

wherein:

T and U, which are the same or different, each represents a —CH— radical or a nitrogen atom so as to form with the pyrimidinyl group a heterocycle selected from: purine, pyrazolo[3,4-d]pyrimidine, pyrrolo[2,3-d]pyrimidine and 1,2,3-triazolo[4,5-d]pyrimidine;

R and R', which are the same or different, each represents an alkyl radical having from 1 to 5 carbon atoms or an alkenyl radical having from 2 to 5 carbon atoms, each in straight or branched chain;

A represents a heteromonocyclic radical of formula:

[Chemical structure]

wherein:

B represents a radical of formula:

$$\diagdown \mkern-6mu CH-O-, \quad \diagdown \mkern-6mu CH-S-, \quad \text{or} \quad \diagdown \mkern-6mu CH-N-\underset{R''}{|},$$

wherein R" is a hydrogen atom or an alkyl radical having from 1 to 5 carbon atoms in straight or branched chain and t represents an integer of from 1 to 3;

p is zero or one;

X and Y, which are the same or different, each represents a hydrogen atom, a halogen atom, or an alkyl or alkoxy radical each having from 1 to 5 carbon atoms in straight or branched chain;

m and n, which are the same or different, each represents an integer of from 1 to 3;

$R_1$ and $R_2$, which are the same or different, each represents a hydrogen atom or an alkyl radical having from 1 to 5 carbon atoms in straight or branched chain, or together represent a single bond, an oxygen or sulphur atom, a radical —$(CH_2)_r$— in which r represents an integer of from 1 to 3, a radical —CH=CH—, —O—$CH_2$—, —S—$CH_2$—, —$SO_2$—$CH_2$—, —CO—$CH_2$—

$$-CO-N-, \text{ or } -SO_2-N-\\ \phantom{-CO-}|\phantom{N,\text{ or }-SO_2-}| \\ \phantom{-CO-}R'''\phantom{,\text{ or }-SO_2-}R'''$$

in each of which R''' represents a hydrogen atom or an alkyl radical having from 1 to 5 carbon atoms in straight or branched chain, or $R_1$ and $R_2$ together represent the radical $$-SO_2-N-\\ |\\ CH_2-CH_2-CH_2-$$

in which the terminal $CH_2$ is attached to the closest carbon of the adjoining benzene ring so that the whole:

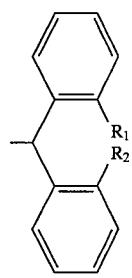

forms the tetracyclic radical of formula:

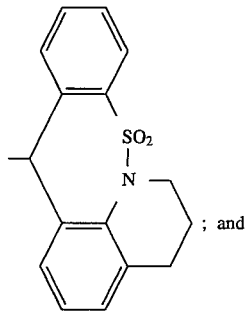; and $R_3$ represents a hydrogen atom or a phenyl radical; and also to the chiral compounds and their enantiomers.

The present invention relates also to a process for the preparation of the compounds of formula I which is characterised in that:

a chlorinated compound of formula II:

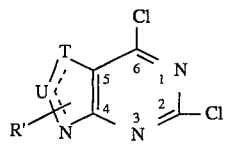 (II)

wherein T, U and R' are as defined above, is condensed with the amine of formula:

$$RNH_2 \quad (III)$$

or

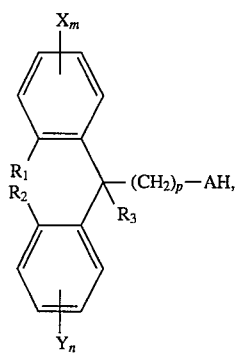 (IV)

whichever it is desired to attach in the 6-position, (R, X, Y, m, n, $R_1$, $R_2$, $R_3$, p and A in those formulae being as defined above), then the product so obtained which, depending on the case concerned, is of formula:

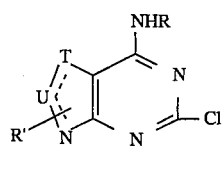 (V)

or

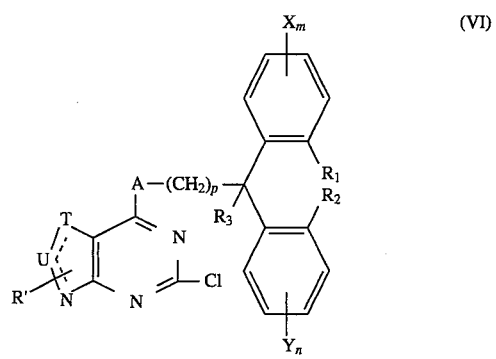 (VI)

is condensed with the other amine of formula III or IV which it is desired to attach in the 2-position—the order of reactivity of the amines with the dichlorinated compounds II being known [cf. Heterocyclic compounds Part II, Ed. D. J. Brown, Wiley-Interscience (1971), Chapter V, p. 160].

Those successive condensations are carried out especially advantageously as follows:

The reaction of compound II with the amine it is desired to attach in the 6-position is carried out in a polar solvent, such as, for example, an alcohol containing from 2 to 5 carbon atoms, dimethylformamide or dimethylacetamide, at a temperature of approximately 60° C., in the presence of an acceptor for the hydracid formed during the course of the reaction; that acceptor may be, for example, triethylamine or an excess of the amine used in the reaction.

The condensation product thus obtained is then condensed with the other amine (to be attached in the 2-position) in a polar solvent of the same type as that used for the preceding condensation, the condensation being carried out in an autoclave at a temperature of from 130° to 150° C. in the presence of an acceptor for the hydracid formed during the course of the reaction; that acceptor may be, for example, triethylamine or an excess of the amine used in the reaction.

The starting materials of formula II were prepared from known dichlorinated compounds, such as:

2,4-dichloropyrrolo[2,3-d]pyrimidine (cf. ROBINS R. K. et al., JACS (1984) 106, 6379);

5,7-dichlorotriazolo[4,5-d]pyrimidine (cf. BITTERLI P., ERLENMEYER H., Helv. Chem. Acta (1951) 34, 835), and 4,6-dichloropyrazolo[3,4-d]pyrimidine (cf. ROBINS R. K., JACS (1957) 79, 6407).

Those dichlorinated compounds, which correspond to the formula:

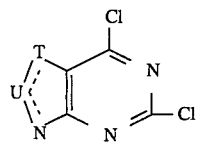

are then reacted with an alcohol of formula:

*R'-OH* in which R' is as defined hereinbefore, according to the Mitsunobu method—Synthesis (1981), 1, by analogy with M. IWAKAWA et al, Can. J. Chem. (1978) 56, 326, and TOYOTA A. et al, Chem. Pharm. Bull. (1992), 40, 1039—to yield the starting materials of formula II.

In certain cases, substitution isomers may be obtained, which may be separated by chromatography.

The compounds of formula I may be converted into addition salts with acids, which salts, as such, form part of the present invention. There may be mentioned as acids that can be used for the formation of those salts, for example, in the inorganic series hydrochloric, hydrobromic, sulphuric, nitric and phosphoric acid and, in the organic series, acetic, propionic, maleic, fumaric, tartaric, oxalic, benzoic, methanesulphonic and isethionic acid.

The compounds of formula I may be purified by physical methods, such as recrystallisation of the bases or salts, chromatography (especially flash chromatography on silica 35-70 μ eluted with ethyl acetate or the system $CH_2Cl_2$/methanol or $CH_2Cl_2$/acetone), or by chemical methods, such as the formation of addition salts with acids and decomposition of those salts with alkaline agents.

The compounds of formula I and their physiologically tolerable addition salts have valuable pharmacological and therapeutic properties, and in particular they partially or completely reverse the resistance of tumour cells to anticancer agents, which allows them to be used as adjuvants in the treatment of cancers with the aim of reducing or suppressing the resistance of the tumour cells to the anti-cancer agents.

The present invention relates also to pharmaceutical compositions comprising as active ingredient a compound of formula I or a physiologically tolerable salt thereof, mixed with or in association with an appropriate pharmaceutical excipient.

The so-obtained pharmaceutical compositions are generally presented in dosage form and may comprise from 0.1 to 1000 mg of active ingredient. They may be, for example, in the form of tablets, dragées, gelatin capsules, suppositories or injectable or drinkable solutions, and may be administered by the oral, rectal or parenteral route.

The dosage varies, especially in accordance with the age and weight of the patient, the route of administration, the nature of the disorder and associated treatments, and ranges from 0.1 to 1000 mg of active ingredient per administration.

The following Examples illustrate the invention. The melting points are determined using a capillary tube (cap) or a Kofler hot plate (K).

Example 1

9-allyl-6-allylamino-2-{4-[(10,11-dihydro-5H-dibenzo-[a,d]cyclohepten-5-yl)methylamino]piperidino}purine

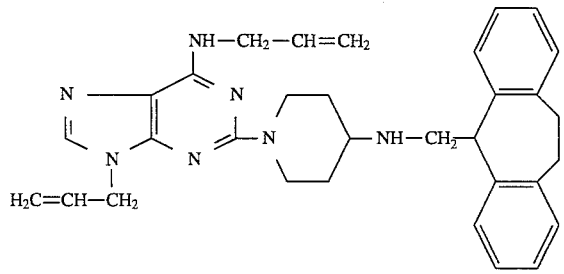

0.75 ml of allylamine is added to a solution of 1.15 g of 2,6-dichloro-9-allylpurine in 15 ml of ethanol and the mixture is stirred for 1 hour at room temperature and then heated at 50° C. for 30 minutes. After evaporation of the solvent, the mixture is taken up in $CH_2Cl_2$-$H_2O$, decanted, and the solvent is evaporated. The residue is recrystallised from ethanol. 1 g of 2-chloro-6-allylamino-9-allylpurine, melting at 110°–112° C. is obtained. 0.85 g of that compound is dissolved in 20 ml to butanol, 1.04 g of 4-[(10,11-dihydro- 5H-dibenzo[a,d]cyclohepten-5-yl)methylamino]-piperidine (oil), 0.5 g of $K_2CO_3$ and 0.1 g of potassium iodide are added to the solution obtained, and the mixture is heated at reflux for 10 hours. The reaction mixture is then concentrated and the residue is taken up in $CH_2Cl_2$-$H_2O$. The mixture is decanted, the organic phase is then evaporated, and the residue is chromatographed using ethyl acetate as eluant. 0.6 g of 9-allyl-6-allylamino-2-{4-[(10,11-dihydro-5H-dibenzo[a,d]cyclohepten-5-yl) methylamino]piperidino}-purine is isolated in the form of crystals melting (cap) at 142°–144° C. The 9-allyl-2,6-dichloropurine used as starting material was prepared by reacting allyl alcohol and 2,6-dichloropurine in tetrahydrofuran according to the Mitsunobu method. The amine used as starting material was prepared by debenzylation of the corresponding piperidine melting at 78°–81° C., which was itself prepared by reductive alkylation with $NaBH_3CN$, in methanol, of a mixture of 1-benzylpiperidone and (10,11-dihydro-5H-dibenzo[a,d] cyclohepten-5-yl)methylamine hydrochloride melting (cap) at 275°–280° C.

Example 2

9-allyl-2-allylamino-6-{4-[(10,11-dihydro-5H-dibenzo-[a,d]cyclohepten-5-yl)methylamino]piperidino}purine

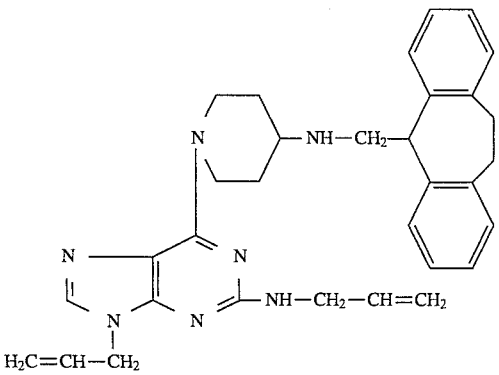

3 g of 4-[(10,11-dihydro-5H-dibenzo[a,d]cyclohepten-5-yl)methylamino]piperidine are added to a solution of 1.15 g of 9-allyl-2,6-dichloropurine in 20 ml of ethanol and the mixture is stirred for 3 hours at room temperature and then for 30 minutes at 50° C. The mixture is then treated as described in Example 1. The residue obtained is recrystallised from ether. 1.8 g of white crystals melting (cap) at 146°–148° C. are obtained. By proceeding as in Example 1, starting from 1.8 g of the 2-chloropurine compound so obtained dissolved in 20 ml of butanol and heated to 150° C. in the presence of 0.6 ml of allylamine, 0.7 g of 9-allyl-2-allylamino-6-{4-[(10,11-dihydro-5H-dibenzo [a,d]cyclohepten-5-yl)methylamino]piperidino}purine is obtained in the form of a resinous product of which the difumarate, recrystallised from ethanol, melts (cap) at 191°–194° C.

Examples 3 to 28

The following compounds were prepared by applying the method described in the above Examples:

3) 9-allyl-6-allylamino-2-{4-[2,2-bis(4-fluorophenyl)-ethylamino]piperidino}purine, m.p. (cap): 143°–145° C.

4) 9-allyl-2-allylamino-6-{4-[2,2-bis(4-fluorophenyl)-ethylamino]piperidino}purine, m-p. (cap) of the corresponding dimaleate: 151°–152° C.

5) 9-allyl-6-allylamino-2-{4-[(6,11-dihydrodibenzo[b,e]oxepin-11-yl)methylamino]piperidino}purine, m.p. (K) of the corresponding fumarate: 240° C.

6) 9-allyl-6-allylamino-2-{4-[(5H-dibenzo[a,d]cyclohepten-5-yl)methylamino]piperidino}purine, m.p. (K) of the corresponding fumarate: 250° C.

7) 6-allylamino-2-{4-[(10,11-dihydro-5H-dibenzo[a,d]cyclohepten-5-yl)methylamino]piperidino}-9-propylpurine, m.p. (K) of the corresponding fumarate: 237° C.

8) 9-allyl-2-{4-[(10,11-dihydro-5H-dibenzo[a,d]cyclohepten-5-yl)methylamino]piperidino}-6-propylaminopurine, m.p. (K) of the corresponding fumarate: 213° C.

9) 1-allyl-4-allylamino-6-{4-[(10,11-dihydro-5H-dibenzo[a,d]cyclohepten-5-yl)methylamino]piperidino}pyrazolo[3,4-d]pyrimidine, m.p. (cap) of the corresponding fumarate: >230° C. with decomposition.

10) 7-allyl-4-allylamino-2-{4-[(10,11-dihydro-5H-dibenzo[a,d]cyclohepten-5-yl)methylamino]piperidino}pyrrolo[2,3-d]pyrimidine, m.p. (cap) of the corresponding fumarate: 160°–163° C.

11) 3-allyl-7-allylamino-5-{4-[(10,11-dihydro-5H-dibenzo[a,d]cyclohepten-5-yl)methylamino]piperidino}1,2,3triazolo[4,5-d]pyrimidine, m.p. (cap) of the corresponding fumarate: 159°–162° C.

12) 9-allyl-6-allylamino-2-{4-[(2,2-diphenylethyl)amino]piperidino}purine, m.p. (K): 150° C.

13) 9-allyl-6-allylamino-2-{4-[(3-chloro-6-methyl-5,5-dioxo-6,11-dihydrodibenzo)[c,f][1,2]thiazepin-11-yl)methylamino]piperidino}purine, m.p. (K) of the corresponding fumarate: 174° C.

14) 9-allyl-6-allylamino-2-{4-[(2-methoxy-10,11-dihydro-5H-dibenzo[a,d]cyclohepten-5-yl)methylamino]piperidino}purine, m.p. (K) of the corresponding fumarate: 205° C.

15) (+)—(R)— or —(S)-9-allyl-6-allylamino-2-{4-[(3-chloro-6-methyl-5,5-dioxo-6,11-dihydrodibenzo[c,f][1,2]thiazepin-11-yl)amino]piperidino)purine, m.p. (K) of the corresponding dihydrochloride: 174° C.

16) (–)—(R)— or —(S)-9-allyl-6-allylamino-2-{4-[(3-chloro-6-methyl-5,5-dioxo-6,11-dihydrodibenzo[c,f][1,2]thiazepin-11-yl)amino]piperidino}purine, m.p. (K) of the corresponding dihydrochloride: 210° C.

17) 9-allyl-2-allylamino-6-{4-[(3-chloro-6-methyl-5,5-dioxo-6,11-dihydrodibenzo[c,f][1,2]thiazepin-ll-yl)methylamino]piperidino}purine, m.p. (K) of the corresponding dihydrochloride: 210° C.

18) 9-allyl-2-allylamino-6-{4-[(6,11-dihydrodibenzo[b,e]oxepin- 11-yl)methylamino]piperidino}purine, m.p. (K) of the corresponding difumarate: 186° C.

19) 9-allyl-2-allylamino-6-{4-[(2-methoxy-10,11-dihydro-5H-dibenzo[a,d]cyclohepten-yl)methylamino]piperidino}purine, m.p. (K) of the corresponding difumarate: 188° C.

20) 9-allyl-2-allylamino-6-{4-[(5H-dibenzo[a,d]cyclohepten-5-yl)methylamino]piperidino)purine, m.p. (K) of the corresponding difumarate: 200° C.

21) 9-allyl-6-allylamino-2-{4-[(11-methyl-10,10-dioxo-5,11-dihydro-10-thia-11-azadibenzo[a,d]cyclohepten-5yl)amino]piperidino}purine, m.p. (K): 182° C.

22) 9-allyl-6-allylamino-2-{4-[(10,10-dioxo-11-propyl-5,11-dihydro-10-thia-11-azadibenzo[a,d]cyclohepten-5yl)methylamino]piperidino}purine, m.p. (K): 165° C.

23) 9-allyl-6-allylamino-2-{4-[(2,3,4-trimethoxy-10,11-dihydro-5H-dibenzo[a,d]cyclohepten-5-yl)methylamino]piperidino}purine, m.p. (K) of the corresponding fumarate: 170° C.

24) 9-allyl-6-allylamino-2-{4-[(6,11-dihydrodibenzo[b,e]oxepin-11-yl)amino]piperidino}purine, m.p. (K) of the corresponding fumarate: 223° C.

25) 9-allyl-6-allylamino-2-{4-[(5,11-dihydro-6-oxodibenzo[b,e]azepin-11-yl)methylamino]piperidino}purine, m.p. (K) of the corresponding fumarate: 240° C.

26) 9-allyl-6-allylamino-2-{4-[(10,11-dihydro-5H-dibenzo[a,d]cyclohepten-5-yl)amino]piperidino}purine, m.p. (K): 114° C.

27) 9-allyl-2-allylamino-6-{4-[(10,11-dihydro-5H-dibenzo[a,d]cyclohepten-5-yl)amino]piperidino)purine, m.p. (K) of the corresponding fumarate: 170° C.

28) 9-allyl-6-allylamino-2-{4-[(2,2,2-triphenylethyl)amino]piperidino}purine, m-p. (K): 175° C.

Example 29: PHARMACOLOGICAL STUDY

Resistance to anti-cancer agents is a major obstacle to the effectiveness of anti-tumour drugs. Of the different types of resistance, "Multidrug Resistance" (MDR) is particularly interesting, since it is induced by compounds of natural origin that are active against solid tumours (anthracyclines, vinca alkaloids, epipodophyllotoxins for example) and is very frequent in certain cancers (colon, for example). When tumour cells are exposed in vitro or in vivo to one of those drugs they become resistant, to varying degrees, to all of those compounds. The resistance phenomenon is as a result of the action of an inducible membrane protein, P-gP 170, the role of which is to increase the efflux of the cytotoxic agent, thus reducing its intracellular concentration, which results in the loss of sensitivity of those cells to the drug. Some medicaments, used in other pathologies, are known to reverse that resistance partially or completely (Tsuruo T., Mechanisms of multidrug resistance and implications for therapy. int. J. Cancer Res., 79, 285–296, 1988; Rothenberg, M. and Ling V., Multidrug resistance: molecular biology and clinical relevance, J.N.C.I., 81, 907–910, 1989; Gottesman M. M. and Pastan, I., Resistance to multiple chemotherapeutic agents in human cancer cells, Trends Pharmacol. Sci., 9, 54–58, 1989; Endicott J. A. and Ling V., The biochemistry of P-glycoprotein-mediated multidrug resistance, Annu. Rev. Biochem., 58,137–171, 1989). When the modulating agent is added at the same time as the cytotoxic agent, it reduces or completely suppresses. MDR-type resistance. Certain medicaments, such as verapamil, amiodarone or cyclosporin, have been used clinically to overcome that resistance, but their intrinsic pharmacological properties and their toxicity limit their use considerably. This gives rise to the interest in searching for compounds that reverse the MDR phenotype but that do not have other pharmacological properties and that are non-toxic. The pharmacological study of the compounds of the present invention consisted first of all in an evaluation in vitro carried out on resistant cells. The parameter measured is the cytotoxicity of the anti-tumour drug, quantified in the absence and in the presence of the reversing compound. Also measured was the effect of the compounds on the intracellular concentration of the cytotoxic agent. In effect, the known compounds for reversing MDR act by increasing the intracellular concentration of cytotoxic agent. This effect is the consequence of inhibiting the action of P-gP 170 which is responsible for the efflux of the drug. This study was completed by an in vivo study, using a murine leukaemia resistant to vincristine (P388/VCR) and using the compounds in association with vincristine.

Material and methods:

1) Activity in vitro

Cytotoxicity

Two resistant cell lines were used:

a Chinese hamster lung line, DC-3F/AD, the resistance of which was induced by actinomycin D. Its resistance factor is greater than 10,000, and it is thus an extremely resistant line.

and a human line from an epidermoid carcinoma of the mouth, KB-A1, the resistance of which was induced by adriamycin (ADR). Its resistance factor is approximately 300.

These two lines are also resistant to vinca alkaloids (vincristine and vinblastine). The cells are cultivated in a complete culture medium (RPMI 1640), containing 10 % foetal calf serum, 2 mM glutamine; 50 units/ml penicillin, 50 µg/ml streptomycin, 10 mM Hepes. The cells are distributed on microplates and exposed to the cytotoxic compound (actinomycin D or adriamycin) at 9 concentrations (2 by 2 series dilutions). The compounds tested for their capacity to reverse MDR are added at the same time as the cytotoxic agent. The cells are then incubated for 4 days. The number of viable cells is then quantified by a colorimetric assay, the Microculture Tetrazolium Assay (Carmichael J., DeGraff W. G., Gazdar A. F., Minna J. D. and Mitchell J. R. Evaluation of a tetrazolium-based semiautomated colorimetric assay: assessment of chemosensitivity testing, Cancer Res., 47, 936–942, 1987). The results are expressed as $IC_{50}$, the concentration of cytotoxic agent that inhibits the proliferation of the treated cells by 50% compared with the control. The results are expressed as a reversion factor (RF):

$$RF = \frac{IC_{50} \text{ cytotoxic agent only}}{IC_{50} \text{ cytotoxic agent in the presence of the reversing compound}}$$

Flow cytometry

Certain anti-cancer compounds such as adriamycin (ADR) exhibit the property of being fluorescent after excitation by a light source of known wavelength. By measuring that fluorescence, it is thus possible to obtain a relative measurement of the intracellular concentration of ADR. Flow cytometry (FCM) is a preferred method of carrying out this kind of measurement and thus determining quickly if certain active compounds act by increasing the intracellular concentration of ADR. The resistant cell line used is KB-A1. The cells ($500 \times 10^3$ per ml) were exposed simultaneously to ADR at a fixed concentration (50 µM) and to the tested compounds at various concentrations. After 5 hours' incubation, the intracellular accumulation of ADR was evaluated by FCM. The analyses were carried out on a flow cytometer ATC3000 (BRUKER-FRANCE) fitted with a 2025 argon laser (SPECTRA-PHISICS-FRANCE) optimised at 488 nm for a capacity of 600 mW. The analysis of each of the samples was carried out on a total of 10,000 cells at a rate of 1,000 cells per second. The results were presented in the form of linear histograms of the intracellular ADR fluorescence.

Expression of the results: for each of the histograms the mean fluorescence per channel (MEAN) was determined by the information system of the apparatus. For all experiments:

a negative control (cells without ADR) fixed the autofluorescence threshold.

a positive control (cells with ADR) determined the MEAN value=MN1.

the "test" tubes (cells with ADR and with compound) were used to determine, for each of the compounds and at each of the concentrations, the MEAN values=MN2.

The results are expressed in the form of variations from the mean fluorescence obtained for each of the "test" tubes (MN2) in relation to the mean fluorescence obtained with the positive control (MN1): VAR-MEAN=MN2-MN1. The parameter expressed is thus the increase in ADR fluorescence in the presence of the tested compounds 2) Activity in vivo Anti-tumour activity The sensitive parent line P388 (murine leukaemia) and the sub-line resistant to vincristine, P388/VCR, were supplied by NCI (Frederick, USA). The tumour cells ($10^6$ cells) were inoculated on day 0 into the intraperitoneal cavity of female B6D2F1 mice (Iffa Credo, France) weighing from 18 to 20 g (groups of 8 to 10 animals). In the case of i.p. administration of the compounds to be tested, the animals received on days 1, 5 and 9:

administration by the i.p. route of 25, 50 or 75 mg/kg of the compound of the present invention to be tested, then 30 to 60 minutes later, an administration by the i.p. route of 0.50 mg/kg of vincristine (used as a reference anti-tumour agent).

In the case of p.o. administration of the compounds to be tested, the animals received on days 1, 2, 3 and 4:

an administration by the oral route of 100 mg/kg of the compound of the present invention to be tested, then 30 to 60 minutes later, an administration by the i.p. route of 0.25 mg/kg of vincristine.

The anti-tumour activity is expressed as follows:

$$\frac{T}{C}\% = \frac{\text{Median survival time of the treated animals}}{\text{Median survival time of the control animals}} \times 100$$

The activity of the reversing compound is expressed as T/V:

$$\frac{T}{V} = \frac{\text{Median survival time of the treated animals with VCR and reversing compound in association}}{\text{Median survival time of the control animals treated with VCR only}}$$

Results

1) Activity in vitro

Table 1 gives the reversion factor values obtained with the various compounds with the line DC-3F/AD and also the increase in the ADR fluorescence (VAR-MEAN) obtained with the various compounds with the line KB-A1. The compounds are far more active than the reference compounds.

Table 2 shows the reversion factor values obtained with the various compounds with the line KB-A1. The compounds of the invention are very active, some of them even far more active than the reference compounds, and completely reverse the resistance of KB-A1 (human cancer line) to adriamycin.

2) Activity in vivo

Table 3 shows the increase in anti-tumour activity of vincristine in vivo obtained with two representative compounds of the present invention. The compounds of Examples 1 and 2 of the invention administered i.p. substantially increase the anti-tumour activity of vincristine against a resistant tumour, vincristine thus exhibiting the same activity as against a sensitive tumour.

Table 4 shows the anti-tumour activity of the compounds of the present invention, administered p.o., on the line P388/VCR.

The compounds of the invention are very active even when administered by the oral route. The most active compounds totally restore the anti-tumour activity of vincristine.

ACTIVITY IN VITRO

TABLE 1

| COMPOUNDS | REVERSION FACTOR 5 μM DC-3F/AD | INTRACELLULAR ACCUMULATION OF ADRIAMYCIN VAR-MEAN at 5 μM KB-A1 |
|---|---|---|
| REFERENCE COMPOUNDS | | |
| verapamil | 3 | 13 |
| cyclosporin A | 4 | 23 |
| COMPOUNDS OF THE EXAMPLES | | |
| 1 | 5173 | 110 |
| 2 | 3368 | 111 |

TABLE 2

| COMPOUNDS | REVERSION FACTOR 5 μM KB-A1 |
|---|---|
| REFERENCE COMPOUNDS | |
| verapamil | 26 |
| cyclosporin A | 285 |
| COMPOUNDS OF THE EXAMPLES | |
| 5 | 572 |
| 9 | 192 |
| 12 | 450 |
| 13 | 458 |
| 19 | 309 |
| 21 | 330 |
| 23 | 339 |
| 25 | 521 |
| 28 | 464 |

ACTIVITY IN VIVO

TABLE 3

Increase in the anti-tumour activity of VCR caused by the compounds of the present invention, administered i.p., on the line P388/VCR

| COMPOUNDS TESTED | DOSE (mg/kg) i.p. | T/C % | T/V |
|---|---|---|---|
| No compound (VCR only) | — | 140 | 1 |
| Example 1 | 25 | 215 | 1.54 |
| | 50 | 239 | 1.71 |
| | 75 | 176 | 1.26 |
| Example 2 | 25 | 192 | 1.37 |
| | 50 | 224 | 1.60 |
| | 75 | 235 | 1.68 |

TABLE 4

Increase in the anti-tumour activity of VCR caused by the compounds of the present invention, administered p.o., on the line P388/VCR

| COMPOUNDS TESTED | DOSE (mg/kg) p.o. | T/C | T/V |
|---|---|---|---|
| No compound (VCR only) | — | 121 | 1 |
| Compounds of the Examples | | | |
| 1 | 100 | 209 | 1.73 |
| 2 | " | 172 | 1.42 |
| 3 | " | 203 | 1.68 |
| 5 | " | 196 | 1.62 |
| 6 | " | 188 | 1.55 |
| 9 | " | 161 | 1.33 |
| 12 | " | 192 | 1.59 |
| 14 | " | 202 | 1.67 |
| 15 | " | 157 | 1.30 |

We claim:

1. Bicyclic pyrimidine compounds selected from those of formula I:

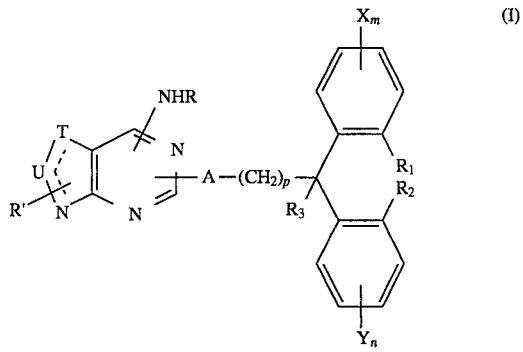

wherein:

T and U, which are the same or different, each represents a —CH— radical or a nitrogen atom so as to form with the pyrimidinyl group a heterocycle selected from: purine, pyrazolo[3,4-d]pyrimidine, and 1,2,3-triazolo[4,5-d]pyrimidine;

R and R', which are the same or different, each represents an alkyl radical having 1 to 5 carbon atoms inclusive or an alkenyl radical having 2 to 5 carbon atoms inclusive, each in straight or branched chain;

A represents a heteromonocyclic radical of formula:

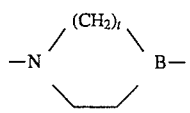

wherein:

B represents a radical of formula:

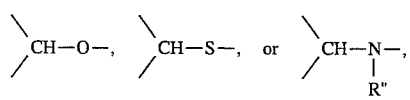

wherein R" is a hydrogen atom or an alkyl radical having 1 to 5 carbon atoms inclusive in straight or branched chain and t represents an integer of 1 to 3; inclusive p is zero or one;

X and Y, which are the same or different, each represents a hydrogen atom, a halogen atom, or an alkyl or alkoxy radical each having 1 to 5 carbon atoms inclusive in straight or branched chain;

m and n, which are the same or different, each represents an integer of 1 to 3 inclusive;

$R_1$ and $R_2$, which are the same or different, each represents a hydrogen atom or an alkyl radical having 1 to 5 carbon atoms inclusive in straight or branched chain, or together represent a single bond, an oxygen or sulphur atom, a radical —$(CH_2)_r$— in which r represents an integer of 1 to 3 inclusive, a radical —CH=CH—, —O—$CH_2$—, —S—$CH_2$—, —$SO_2$—$CH_2$—, or —CO-$CH_2$—, $R_3$ represents a hydrogen atom or a phenyl radical; and the chiral compounds and their enantiomers, and their physiologically tolerable salts with appropriate acids.

2. A compound of claim 1, which is 9-allyl-6-allylamino-2-{4-[(10,11-dihydro-5H-dibenzo[a,d]cyclohepten-5-yl)methylamino]piperidino}purine.

3. A compound of claim 1, which is 9-allyl-6-allylamino-2-{4-[2,2-bis(4-fluorophenyl)ethylamino]piperidino}purine.

4. A compound of claim 1, which is selected from 9-allyl-6-allylamino-2-{4-[(6,11-dihydrodibenzo[b,e]oxepin-ll-yl)methylamino]piperidino}purine and its corresponding fumarate.

5. A compound of claim 1, which is selected from 9-allyl-6-allylamino-2-{4-[(5H-dibenzo[a,d]cyclohepten-5-yl)methylamino]piperidino}purine and its corresponding fumarate.

6. A compound of claim 1, which is selected from 1-allyl-4-allylamino-6-{4-[(10,11-dihydro-5H-dibenzo[a,d]cyclohepten-5-yl)-methylamino]piperidino}pyrazolo[3,4-d]pyrimidine and its corresponding fumarate.

7. A compound of claim 1, which is 9-allyl-6-allylamino-2-{4-[(2,2-diphenylethyl)amino]piperidino}purine.

8. A compound of claim 1, which is selected from 9-allyl-6-allylamino-2-{4-[(2-methoxy-10,11-dihydro-5H-dibenzo[a,d]cyclohepten-5-yl)methylamino]piperidino}purine and its corresponding fumarate.

9. A compound of claim 1 which is selected from 9-allyl-2-{4-[(10,11-dihydro-5H-dibenzo[a,d]cyclohepten-5-yl)methylamino]piperidino}-6-propylaminopurine and its corresponding fumarate.

10. A compound of claim 1 which is selected from those of the formula I':

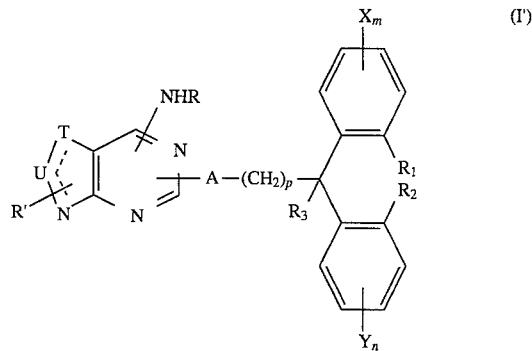

wherein:

—T and U, which are different, each represents —CH— or nitrogen so as to form with the pyrimidinyl group a heterocycle selected from purine and pyrazolo [3,4-d] pyrimidine, —R represents: —$CH_2$—CH=$CH_2$ or —$CH_2$—$CH_2$-$CH_3$ —R' is —$CH_2$—CH=$CH_2$ substituted on a ring nitrogen atom —A represents

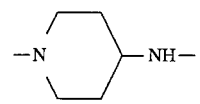

—p is 1

—$X_m$ and $Y_n$ are H

—$R_s$ is H

—and $R_1R_2$ together represent: —$CH_2$—$CH_2$.

11. A pharmaceutical composition useful to suppress the resistance of tumour cells to anti-cancer agents, comprising as active ingredient a compound of claim 1 together with an effective amount of one or more appropriate pharmaceutical excipients.

12. A method of treating a "mammal" the condition of which necessitates the suppression of the MDR type of resistance of tumour cells to anti-cancer agents, which comprises administering to the said mammal an effective dose of a of claim 1 required to effect the said suppression in the mammal concerned.

* * * * *

UNITED STATES PATENT AND TRADEMARK OFFICE
CERTIFICATE OF CORRECTION

PATENT NO. : 5,508,277  
DATED : April 16, 1996  
INVENTOR(S) : Gilbert Regnier, Alain Dhainaut, Ghanem Atassi, Alain Pierre Page 1 of 3

It is certified that error appears in the above-indentified patent and that said Letters Patent is hereby corrected as shown below:

Column 2, line 51: Should have a -- , -- (comma) at the end thereof.
Column 2, line 52: Should be a continuation of line 51.

Column 2, line 60: "radica" should read -- radical --.

Column 6, line 5: "to" should read -- of --.
Column 6, line 6: Delete the space before "5H".

Column 7, lines 9,15,19,23,27,37,57 and 61: Delete excess space in each line.
Column 7, line 20: "dibenzol[     a.d]": delete the space before "a.d]".
Column 8, line 3: "5yl)" should read -- 5-yl) --.

Column 8, lines 11,16,19, and 22: Delete excess space before "9-allyl-" in each line.
Column 8, line 44: "int." should read -- Int. --.

UNITED STATES PATENT AND TRADEMARK OFFICE
CERTIFICATE OF CORRECTION

PATENT NO. : 5,508,277
DATED : April 16, 1996
INVENTOR(S) : Gilbert Regnier, Alain Dhainaut, Ghanem Atassi, Alain Pierre It is certified that error appears in the above-indentified patent and that said Letters Patent is hereby corrected as shown below:

Column 13, line 18: "1 to 3; inclusive" should read -- 1 to 3 inclusive; --. Claim 1, page 25, line 1: of P.A. dtd 8/10/94.

Column 13, line 31: "1 to 3inclusive," should read -- 1 to 3 inclusive, --. Claim 1, page 25, line 14: of P.A. dtd 8/10/94.

Column 14, line 33: "A represents" should read -- A represents: --. Claim 14, Line 12 of R&A dtd Column 14, line 43: "$-R_6$" should read -- $-R_3$ --. Claim 14, Line 15 of R&A dtd 8/29/95, Column 14, line 44: "$CH_2-CH_2$." should read -- $CH_2-CH_2-$. --. Claim 14, line 16: of R&A dtd 8/29/95, page 3.

UNITED STATES PATENT AND TRADEMARK OFFICE
CERTIFICATE OF CORRECTION

PATENT NO. : 5,508,277
DATED : April 16, 1996
INVENTOR(S) : Gilbert Regnier, Alain Dhainaut, Ghanem Atassi, Alain Pierre It is certified that error appears in the above-indentified patent and that said Letters Patent is hereby corrected as shown below:

Column 14, line 51: "mammal" should read -- mammal, --.
 Claim 12, line 1 of P.A. dtd 8/10/94, page 2.
Column 14, line 55: "dose of a" should read -- dose of a compound --. Pg. 29, line 2

Signed and Sealed this

Sixteenth Day of July, 1996

Attest:

BRUCE LEHMAN

Attesting Officer

Commissioner of Patents and Trademarks